Figure 1:
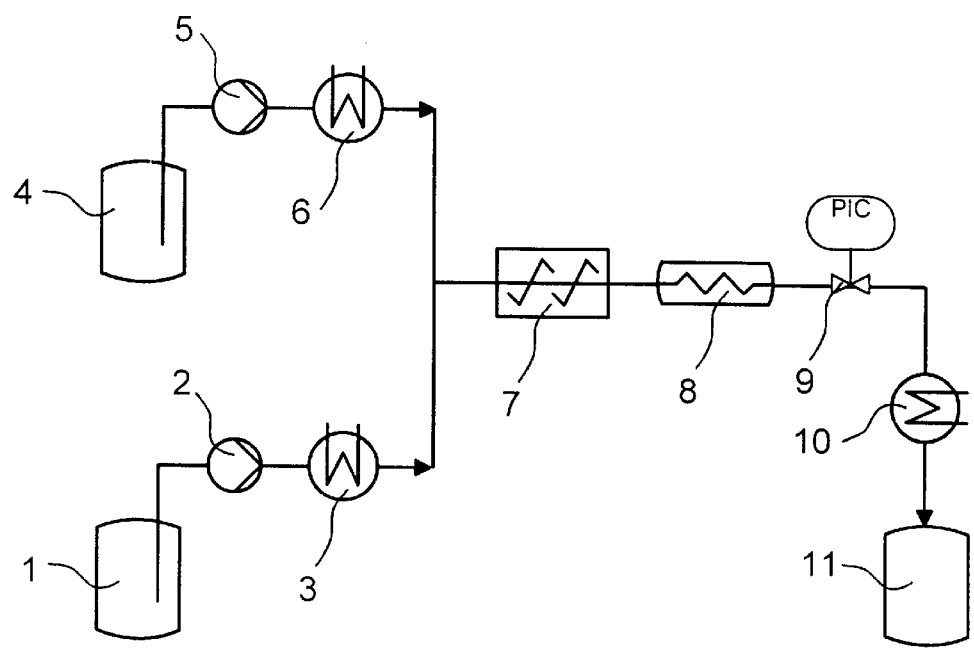

United States Patent [19]
Etzrodt et al.

[11] Patent Number: 6,051,741
[45] Date of Patent: Apr. 18, 2000

[54] PREPARATION OF γ,δ-UNSATURATED KETONES BY THE CARROLL REACTION, NOVEL CATALYSTS THEREFOR AND THE PREPARATION THEREOF

[75] Inventors: Heinz Etzrodt, Neustadt; Dietmar Weller, Ludwigshafen; Carsten Oost, Bad Dürkheim; Hagen Jaedicke, Ludwigshafen; Manfred Stroezel, Ilvesheim; Bernhard Bockstiegel, Römerberg; Lothar Laupichler, Frankenthal; Klaus Reimer, Mutterstadt, all of Germany

[73] Assignee: BASF Aktiengesellschaft, Ludwigshafen, Germany

[21] Appl. No.: 09/168,378

[22] Filed: Oct. 8, 1998

[30] Foreign Application Priority Data

Oct. 17, 1997 [DE] Germany .............................. 197 45 672
Apr. 8, 1998 [DE] Germany .............................. 198 15 810

[51] Int. Cl.$^7$ ...................................................... C07C 45/00
[52] U.S. Cl. ......................... 568/406; 568/383; 568/388; 568/398; 423/625; 554/38; 556/170
[58] Field of Search ..................... 568/383, 388, 568/397, 398, 406, 408; 423/625; 556/38, 170

[56] References Cited

U.S. PATENT DOCUMENTS 2,795,617 6/1957 Kimel et al. ............................ 260/595

FOREIGN PATENT DOCUMENTS 1 247 003 10/1960 France .
1 265 113 5/1961 France .
886353 1/1962 United Kingdom .

OTHER PUBLICATIONS

Walter Kimel, et al., "The Rearrangement of Allyl–Type Esters of β–Keto Acids", J. Am. Chem. Soc., vol. 65, 1943, pp. 1992–1998.

R. K. Mehrotra, et al., "Reactions of Aluminum Alkoxides with Acetylacetone, Benzoylacetone, and Ethyl Acetoacetate", Can. J. Chem., vol. 39, 1961, pp. 795–798.

Walter Kimel, et al. "Total Synthesis of Pseudoionone and an Isomeric Ketone", J. Org. Chem., vol. 23, No. 2, 1958, pp. 153–157.

J. Weichet, et al., "Studies in der Vitamin–K– und Vitamin–E–Reihe XIL,* Synthese von 2–Methyl–3–Difarnesyl–1, 4–Naphthochinon und verwandten Verbindungen", Collect. Czech. Chem. Comm., vol. 25, 1960, pp. 1914–1921.

Primary Examiner—Gary Geist
Assistant Examiner—Sreeni Padmanabhan
Attorney, Agent, or Firm—Oblon, Spivak, McClelland, Maier & Neustadt, P.C.

[57] ABSTRACT

A process for preparing γ,δ-unsaturated ketones of the general formula I

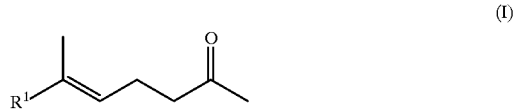

by reacting an allyl alcohol of the general formula II

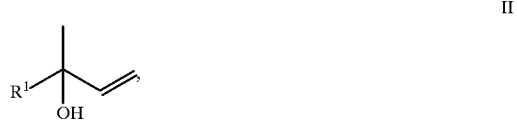

in which $R^1$ is H or a hydrocarbon radical having 1 to 20 carbon atoms, with diketene or an alkyl acetoacetate of the general formula III

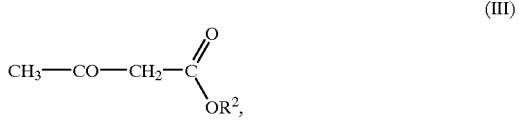

in which $R^2$ is alkyl having 1 to 4 carbon atoms in an unmodified or modified Carroll reaction in the presence of an aluminum catalyst, wherein aluminum compounds which are stable liquids at room temperature, or a mixture of such aluminum compounds, which comprise at least one radical formed from an alkyl acetoacetate and 1 or 2 alkoxy radicals, or else comprise exclusively radicals formed from alkyl acetoacetates, which are esterified with sec-butanol or isobutanol, or else are esterified with at least two different alcohols, are used as aluminum catalyst. Also claimed are the novel mixtures of aluminum compounds which comprise radicals which are formed exclusively from alkyl acetoacetates and are esterified with at least two different alkanols, and the batchwise and continuous preparation of the liquid aluminum catalysts.

23 Claims, 2 Drawing Sheets

PREPARATION OF γ,δ-UNSATURATED KETONES BY THE CARROLL REACTION, NOVEL CATALYSTS THEREFOR AND THE PREPARATION THEREOF

The invention relates to an improved process for preparing γ,δ-unsaturated ketones, in particular methylheptenone, geranylacetone and farnesylacetone or their dihydro derivates, by a Carroll reaction in the presence of novel aluminum catalysts, and to novel suitable aluminum catalysts and their preparation.

A Carroll reaction is the chain extension of an allyl or propargyl alcohol with acetoacetic esters or diketene to form γ,δunsaturated ketones. It may take place, for example, in accordance with the following reaction scheme:

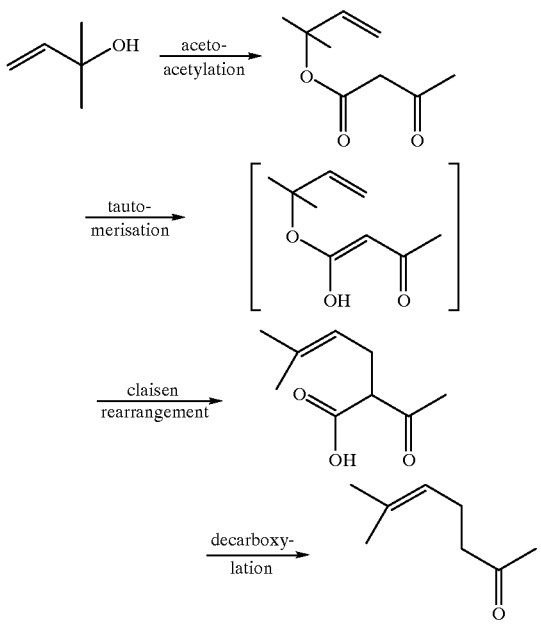

Thus, in the key step, the new acetoacetic ester formed from the allyl or propargyl alcohol and the acetoacetic ester or diketene undergoes a Claisen rearrangement to give the β-keto acid which then spontaneously decarboxylates. The first investigations on Carroll reactions are described in J. Am. Chem. Soc. 65 (1943) 1992–1998.

Since the early 1950s, this reaction has been widely used for preparing terpenes. For example, the terpenes 2-methyl-2-hepten-6-one, geranylacetone and farnesylacetone, which are required as essential precursors for vitamins A and E, are prepared on the industrial scale by a Carroll reaction.

The catalysts used for Carroll reactions in the process of U.S. Pat. No. 2,795,617 were aluminum alcoholates, in particular aluminum isopropoxide of the formula Al(O—CH(CH$_3$)$_2$)$_3$ in amounts of from 0.8 to 2.5 mol-% based on the alcohol employed as starting material.

The catalysts employed for Carroll reactions in the process of GB 886 353 are aluminum complexes with acetylacetone or acetoacetic esters, such as aluminum tri(acetylacetonate), aluminum tri(methyl acetoacetate) or aluminum tri(ethyl acetoacetate), which were obtained by reacting an aluminum salt with an aqueous solution of acetylacetone in ammonia or by reacting aluminum trialkoxides with methyl or ethyl acetoacetate, distilling out the liberated alcohol and isolating the precipitated solid aluminum catalyst. Both the use of ammonia and the solid nature of the aluminum compound are disadvantageous for industrial use.

In a more theoretical treatment by Mehrotra et al. in Can. J. of Chem. 39 (1961), pages 795–798, of aluminum complexes, besides the preparation of aluminum compounds triply complexed with acetylacetone, benzoylacetic esters or acetoacetic esters, there are also descriptions of the preparation of aluminum complexes in which only one or two of the alkoxy radicals of the appropiate aluminum alcoholates are replaced by acetylacetone, benzoyl-acetic ester or acetoacetic ester groups. In these cases, the ligand to be introduced (e.g. ethyl acetoacetate) is mixed with a solution of aluminum triisopropoxide in benzene, and this mixture is refluxed for 3 hours. After the reaction is complete, the resulting alcohol is distilled out as azeotrope with benzene. The process described by Mehrotra is unsuitable for industrial preparation of aluminum compounds. On the one hand, the use of benzene is prohibited for the use of the aluminum compound in further processes such as, for example, for use as catalyst in the preparation of fragrances or precursors of vitamin E. On the other hand, the two-stage process (reaction under reflux+distillation) requires high capital costs and is thus economically unattractive.

The use of these aluminum complexes as catalysts for Carroll reactions is not mentioned therein. Processes on the industrial scale to date have essentially used aluminum triisopropoxide.

One disadvantage of the aluminum catalysts used to date is that they are crystalline compounds which makes it necessary to operate with solids, which is complicated for processes on the industrial scale. An additional disadvantage is that they have only low solubility in the reactants. Thus, for example, the solubility of aluminum tri(methyl acetoacetate) in ethyl acetoacetate at room temperature is only about 4%, and it is virtually insoluble in the starting materials of particular interest in terpene chemisty such as 2-methyl-3-buten-2-ol, linalool or nerolidol.

Aluminum tri-sec-butoxide is liquid under normal conditions and therefore easier to handle but is not employed industrially as catalyst for Carroll reactions because relatively large amounts of byproducts, and therefore less good yields of the required γ,δ-unsaturated ketones, are obtained when it is used.

It is an object of the present invention to develop catalysts for preparing γ,δ-unsaturated ketones which can be prepared easily and are at least as effective as the catalysts known for this reaction, in whose presence only few byproducts are formed, and which, in addition, can be readily handled technically on the industrial scale. For them to be readily handled technically they must result as liquids from the preparation, be stable on storage as such and be pumpable and free-flowing as viscous liquids, where appropriate as melt or mixed with small amounts of a lower alcohol or another inert solvent, so that complicated operations with solids are avoided on the industrial scale.

We have found that these objects are achieved by catalysts for the Carroll reaction with aluminum catalysts which comprise at least one alkyl acetoacetate radical and comprise 1 or 2 alkoxy radicals or else exclusively alkyl acetoacetate radicals, which are esterified with sec-butanol or isobutanol or else with at least two different alkanols having 1 to 10 carbon atoms.

The invention therefore relates to a process for preparing γ,δ-unsaturated ketones of the general formla I

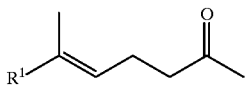
(I)

by reacting an allyl alcohol of the general formula II

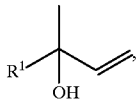
II in which $R^1$ is H or a saturated or unsaturated branched hydrocarbon radical having 1 to 20 carbon atoms, with diketene or an alkyl acetoacetate of the general formula III

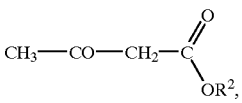
(III)

in which $R^2$ is alkyl having 1 to 5 carbon atoms, in an unmodified or modified Carroll reaction in the presence of an aluminum catalyst, wherein aluminum compounds which are stable liquids at room temperature, or a mixture of such aluminum compounds, which comprise at least one radical formed from an alkyl acetoacetate and 1 or 2 alkoxy radicals, or else comprise exclusively radicals formed from alkyl acetoacetates, which are esterified with sec-butanol or isobutanol, or else are esterified with at least two different alkanols, are used as aluminum catalyst.

Aluminum compounds which are stable liquids at room temperatures and which comprise exclusively radicals formed from acetoacetic esters generally mean aluminum compounds or mixtures of aluminum compounds of the general formula V

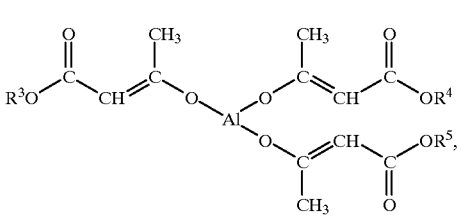
(V)

$R^3$ is an alkyl group having 1–5 carbon atoms, preferably —$CH_3$, —$C_2H_5$ or —$CH(CH_3)$—$C_2H_5$, $R^4$ is an alkyl group having 3 to 10 carbon atoms, preferably —$CH(CH_3)_2$, —$CH(CH_3)$—$C_2H_5$ or —$CH(CH_3)$—$C_3H_7$ and $R^5$ is an alkyl group having 1–10 carbon atoms, preferably —$CH_3$, —$C_2H_5$, —$CH(CH_3)_2$, —$CH(CH_3)$—$C_2H_5$ or —$CH(CH_3)$—$C_3H_7$, where the radicals $R^3$, $R^4$ and $R^5$ may have the same meaning only if all 3 are —$CH(CH_3)$—$C_2H_5$ or —$CH_2$—$CH(CH_3)_2$.

Aluminum compounds which are stable liquids at room temperature and which comprise at least one radical formed from an alkyl acetoacetate and 1 or 2 alkoxy radicals generally mean aluminum compounds of the general formulae IV or VII

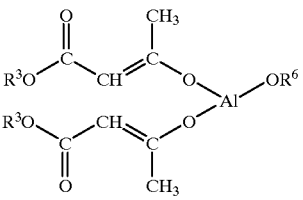
(IV)

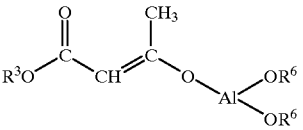
(VII)

in which $R^3$ is an alkyl group having 1–5 carbon atoms, and $R^6$ is an alkyl group having 1–10 carbon atoms.

The process according to the invention takes place particularly advantageously if the aluminum catalysts used are the novel mixtures of aluminum compounds of the general formula V,

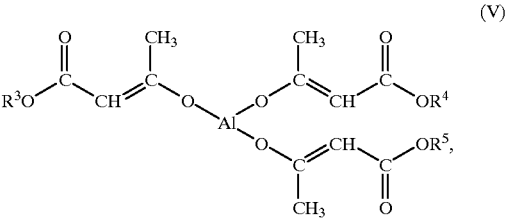
(V)

in which $R^3$ is an alkyl group having 1–5 carbon atoms, preferably —$CH_3$, —$C_2H_5$ or —$CH(CH_3)$—$C_2H_5$, $R^4$ is an alkyl group having 3 to 10 carbon atoms, preferably —$CH (CH_3)_2$, —$CH(CH_3)$—$C_2H_5$, —$C(CH_3)_3$ or —$CH (CH_3)$—$C_3H_7$ and $R^5$ is an alkyl group having 1 to 10 carbon atoms, preferably —$CH_3$, —$C_2H_5$, —$CH(CH_3)_2$, —$CH (CH_3)$—$C_2H_5$ or —$CH (CH_3)$—$C_3H_7$, where the radicals $R^3$, $R^4$ and $R^5$ may not all have the same meaning.

The invention therefore also relates to the novel mixtures of aluminum compounds of the general formula V

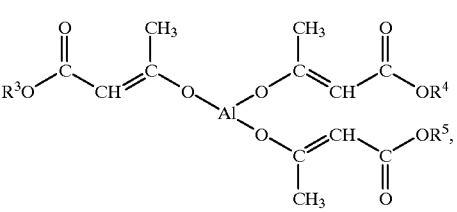
(V)

in which $R^3$, $R^4$ and $R^5$ have the abovementioned meanings, especially mixtures of aluminum compounds of the general formula V in which $R^3$ is —$CH_3$, —$C_2H_5$ or —$CH(CH_3)$—$C_2H_5$, $R^4$ is an alkyl group having 3 to 10 carbon atoms, preferably —$CH (CH_3)_2$, —$CH(CH_3)$—$C_2H_5$, —$C(CH_3)_3$ or —$CH(CH_3)$—$C_3H_7$, and $R^5$ is an alkyl group having 1 to 10 carbon atoms, preferably —$CH_3$, —$C_2H_5$, —CH ($CH_3$)$_2$, —CH ($CH_3$)—$C_2H_5$ or —CH($CH_3$)—$C_3H_7$,
where the radicals $R^3$, $R^4$ and $R^5$ may not all have the same meaning, and to a process for preparing these aluminum compounds.

Suitable allyl alcohols of the general formula II are alcohols such as 2-methyl-but-3-en-2-ol, 3,7-dimethyl-1,6-octadien-3-ol (linalool), 3,7-dimethyl-1-octen-3-ol (6,7-dihydrolinalool), 3,7,11-trimethyl-1,6,10-dodecatrien-3-ol (nerolidol), 3,7,11,15-tetramethyl-1,6,10,14-hexadecatetraen-3-ol (geranyllinalool), 3,7,11,15-tetramethyl-1-hexadecaen-3-ol (isophytol), 3,7,11-trimethyl-1-dodecen-3-ol and 3,7,11-trimethyl-1,6-dodecadien-3-ol (10,11-dihydronerolidol), in particular 2-methyl-3-buten-2-ol, 6,7-dihydrolinalool, linalool, nerolidol and 10,11-dihydronerolidol.

Particularly suitable alkyl acetoacetates of the general formula III for the Carroll reaction of a methyl ester, the ethyl ester, the isopropyl ester, the tert-butyl ester and the sec-butyl ester, in particular the commercially obtainable methyl acetoacetate and ethyl acetoacetate.

The procedure for the Carroll reaction is generally first to add the aluminum catalyst to the allyl alcohol of the formula II and then, at temperatures from 150 to 220° C., to add the acetoacetic ester of the formula III slowly.

For further details of the procedure for Carroll reactions, we refer to W. Kimel et al. in J. Org. Chem. 23 (1958), pages 153–157 and J. Weichert et al. in Collect. Czech. Chem. Comm. 25 (1960), pages 1914 to 1921.

A modified Carroll reaction referred to in this connection is a variant of the Carroll reaction described by Kimel and Sax in J. Org. Chem. 23, 2 (1958), pages 153–157, in which the allyl alcohols of the formula II are reacted with diketene at low temperatures, and then the resulting acetoacetates of the allyl alcohol of the formula II, which are stable up to about 100° C., are rearranged to the γ,δ-unsaturated ketones at temperatures from 150 to 220° C.

The preparation of the aluminum catalysts used according to the invention advantageously starts from aluminum triisopropoxide, aluminum tri-sec-butoxide or aluminum tri-sec-pentoxide, which are in turn prepared in a manner known per se by reacting metallic aluminum with the appropriate alcohol in the presence of suitable catalysts. It is not necessary to employ the aluminum alcoholates in isolated and purified form. Almost equally good results are obtained when the reaction mixture obtained when aluminum is reacted with the appropriate alcohols is used directly.

A procedure for preparing the mixtures of aluminum compounds of the general formulae IV and VII, in which $R^3$ is an alkyl group having 1 to 5 carbon atoms, preferably —$CH_3$ or —$C_2H_5$, $R^6$ is an alkyl group having 2 to 10 carbon atoms, preferably —CH($CH_3$)$_2$, —CH($CH_3$)—$C_2H_5$, —C($CH_3$)$_3$ or —CH($CH_3$)—$C_3H_7$, is advantageously such that aluminum triisopropoxide, aluminum tri-sec-butoxide, aluminum tri-tert-butoxide or aluminum tri-sec-pentoxide, preferably aluminum tri-sec-butoxide, is heated, where appropriate in a solvent such as benzene, with less than 3 mol, preferably 1 to 2 mol, of methyl or ethyl acetoacetate per mole of aluminum alcoholate, without distilling out the liberated alcohol.

The general procedure for preparing the novel mixtures of aluminum catalysts of the general formula V, in which $R^3$ is an alkyl group having 1 to 5 carbon atoms, preferably —$CH_3$ or —$C_2H_5$, $R^4$ is an alkyl group having 3 to 10 carbon atoms, preferably —CH($CH_3$)$_2$, —CH($CH_3$)—$C_2H_5$, —C($CH_3$)$_3$ or —CH($CH_3$)—$C_3H_7$, and $R^5$ is an alkyl group having 1 to 10 carbon atoms, preferably —$CH_3$, —$C_2H_5$, —CH($CH_3$)—$C_2H_5$ or —CH($CH_3$)—$C_3H_7$, where the radicals $R^3$, $R^4$ and $R^5$ may not all have the same meaning,
is such that aluminum alcoholates of the general formula VI

$$Al(O-R^6)_3 \qquad (VI),$$

in which $R^6$ is an alkyl group having 2 to 10 carbon atoms, preferably —CH($CH_3$)$_2$, —CH($CH_3$)—$C_2H_5$, —C($CH_3$) or —CH($CH_3$)—$C_3H_7$, is heated with about 3 to 10 mol, preferably 3 to 5 mol, of an alkyl acetoacetate derived from an alcohol which is different from $R^6$OH and has 1 to 5 carbon atoms, in particular 3 to 5 mol of methyl acetoacetate or ethyl acetoacetate per mole of aluminum alcoholate, without removing the higher alcohol liberated in the reaction during the heating from the reaction mixture. In general, the aluminum alcoholate is heated with the alkyl acetoacetate in a batchwise procedure until refluxing gradually starts.

In order to speed up the reaction, however, the heating can also be carried out in a closed system at higher temperatures, which is particularly important for a continuous procedure. Temperatures which have proven advantageous under elevated pressure are from 100 to 220° C., preferably from 150 to 200° C.

If, for example, aluminum triisopropoxide or aluminum tri-sec-butoxide is heated with at least 3 mol of methyl or ethyl acetoacetate per mole of aluminum alcoholate to temperatures above 100° C. there is spontaneous elimination of the alcohol bound to the aluminum, and there is formation, when the alcohol is distilled off, of the aluminum tri(methyl acetoacetate) or tri(ethyl acetoacetate) of low solubility. If, on the other hand, the alcohol liberated from the aluminum alcoholate during the heating is left in the reaction mixture and heating is continued, then there is partial displacement by this alcohol of one or even two of the alkoxy groups in the initially formed aluminum tri(alkyl acetoacetate). It has emerged, surprisingly, that these not previously described mixtures of aluminum acetoacetates with different ester groups in the molecule do not crystallize but remain stable as viscous liquids for weeks and thus can be handled technically considerably better than, for example, the crystalline aluminum tri(methyl acetoacetate) of low solubility, and nevertheless show an activity which is as good as the latter and is better than that of aluminum triisopropoxide (cf. Example 4a and Comparative Example 4b). The aluminum triacetoacetates prepared in this way are not single compounds. They comprise mixtures of, for example, aluminum di(methyl acetoacetate) mono(sec-butyl acetoacetate) and aluminum mono(methyl acetoacetate) di(sec-butyl acetoacetate). The precondition for the liquid state of aggregation at room temperature over several months proves to be the degree of transesterification, which means in this case the ratio of the number of 2-butoxy groups to the number of all the alkoxy groups, in this case the total of methoxy groups and 2-butoxy groups. It is necessary for more than about every third methoxy group in the aluminum tri(methyl acetoacetate) to be replaced by the sec-amyloxy group, sec-butoxy group, tert-butoxy group or isopropoxy group in order to form the required viscous liquid catalysts.

The novel viscous liquid mixtures of aluminum catalysts of the general formula V in which all the alkoxy radicals of the aluminum trialkoxides have been replaced by at least partly different alkyl acetoacetate radicals can also be obtained by heating the aluminum trialkoxides of the general formula VI with at least 3 mol of a mixture of at least 2 different alkyl acetoacetates, for example of 2 mol of methyl acetoacetate and 1 mol of sec-butyl acetoacetate.

It has furthermore been found, surprisingly, that the liquid aluminum compounds of the general formula V which comprise exclusively radicals formed from acetoacetic esters can very particularly advantagesously be prepared continuously if the pressure and temperature are chosen so that evaporation of the liberated alcohol out of the reaction mixture is impossible.

The invention therefore also relates to a process for the continuous preparation of aluminum compounds which are liquid at room temperature, or mixtures of aluminum compounds, of the general formula V, which comprises continuously reacting in each case one mole of an aluminum alcoholate of the general formula VI with at least 3, preferably 3 to 10, moles of an alkyl acetoacetate of the general formula III or else with at least 3 mol of a mixture of 2 or 3 different alkyl acetoacetates of the general formula III in pure form or dissolved in a suitable solvent at temperatures from 100 to 250° C., preferably 150 to 200° C., under a pressure of from 1 to 100 bar, preferably 1 to 10 bar, and with residence times of from 5 to 120 minutes, preferably 15 to 45 minutes, it being necessary to choose the pressure and temperature so that no gas phase can form in the reaction vessel.

The continuous reaction must surprisingly be carried out as liquid-phase reaction, i.e. a gas phase is, in contrast to the batchwise process, not permitted. The reaction mixture must therefore not boil. If the pressure is too low during the reaction there is formation of a gas phase in which the alcohol with the lower boiling point accumulates. The latter is thereby removed from the equilibrium so that the transesterification reaction takes place only incompletely. This in turn may lead to the aluminum catalyst not being liquid, but precipitating. Accordingly, the pressure must be adjusted so that the pressure-dependent boiling point of the reaction mixture is above the freely selectable reaction temperature.

The reaction comprises a reversible equilibrium reaction with the position of the equilibrium and the rate of setting up equilibrium being dependent on the temperature. The temperature and residence time therefore cannot be set independently of one another. For a given temperature, the residence time must be chosen so that an adequate degree of transesterification is reached. Otherwise there is a risk of the catalyst precipitating.

The degree of transesterification surprisingly increases quadratically with the temperature but only linearly with the residence time. A change in the temperature therefore has a considerably greater effect on the degree of transesterification than does the residence time.

At high temperature with a long residence time, a state of equilibrium is reached. For a given temperature, it is therefore only worthwhile to choose the residence time at which the state of equilibrium or the required degree of transesterification is just reached. A further increase in the residence time has no effect on the reaction and thus leads only to a reduction in the space-time yield.

The procedure for the continuous preparation of the liquid aluminum compounds of the general formula V is advantageously that depicted diagrammatically in FIG. 1 (FIG. 1). In this, the alkyl acetoacetate of the general formula III is pumped by a pump 2 out of a receiving vessel 1, and the aluminum alcoholate of the general formula VI or a solution of this alcoholate is pumped by a pump 5 out of a receiving vessel 4 into the mixer 7. It is advantageous for the two reactants to be preheated or even brought to the reaction temperature by means of the heat exchangers 3 and 6 respectively. The mixer 7 must be operated at elevated temperature and elevated pressure. After the reactants have been mixed in mixer 7, the continuous reaction advantageously takes place in a reactor 8 with tubular characteristics. The reaction system is kept at the required pressure by means of a pressure controller 9, it being necessary to choose the pressure and the temperature such that evaporation of the alcohol liberated from the aluminum alcoholate is impossible. The reaction mixture leaving the reactor is decompressed to atmospheric pressure, cooled by means of the heat exchanger 10 and collected in a receiving vessel 11.

The invention accordingly also relates to a process for the continuous preparation of the aluminum compounds of the general formula V as is described above, wherein the aluminum alcoholate of the general formula VI is mixed with the alkyl acetoacetate or the alkyl acetoacetates of the general formula III continuously under elevated pressure and at elevated temperature in a mixer and then reacted in a reactor with tubular characteristics.

Figure 2:
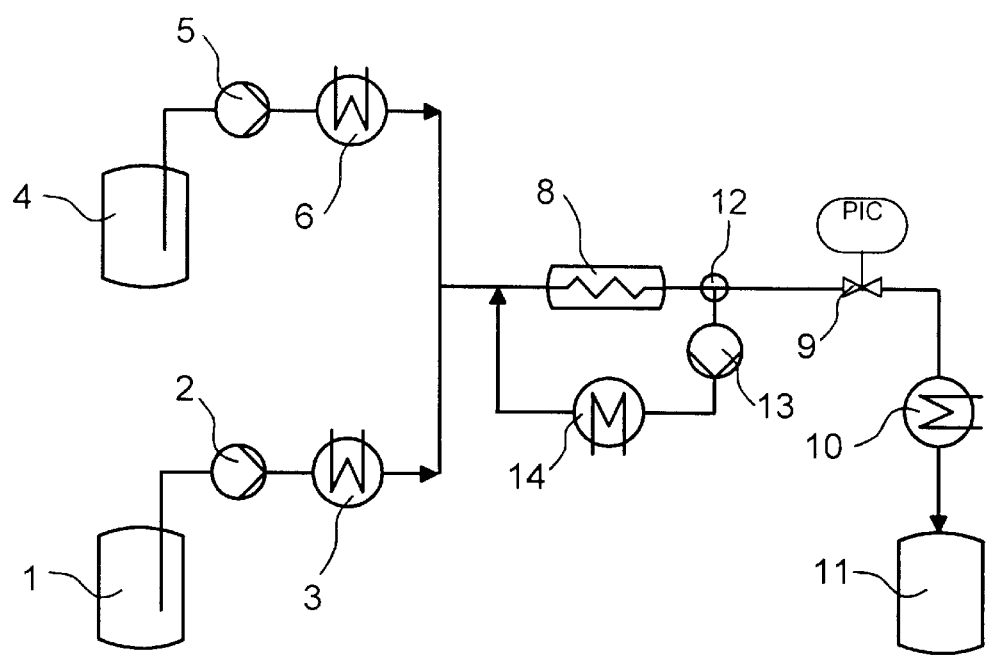

An alternative possibility to this preferred embodiment is to carry out the continuous reaction in a so-called loop reactor or recycle reactor, which may mean in practice that the reaction can be carried out in a flow tube reactor with external circulation, as depicted diagrammatically in FIG. 2 (FIG. 2). In this, the reaction discharge leaving the reactor 8 is returned through a three-way tap 12 by a pump 13, where appropriate through a heat exchanger 14, to the reactor inlet. It is possible in this case to dispense with an upstream mixer 7.

In place of the tubular reactor or the loop reactor, however, it is also possible in principle to carry out the continuous reaction in a stirred vessel or in a cascade of stirred vessels.

The alcohol liberated in the reaction can, after the reaction is complete, be removed from the reaction mixture by one-stage distillation, for example using a thin-film evaporator.

If the liberated alcohol is left in the reaction mixture after the end of the reaction, the resulting solution generally has good flow characteristics and pumpability.

To achieve better flow characteristics or pumpability, however, it is also possible to add small amounts, i.e. amounts of from 20 to 100% by weight, of a lower alcohol or another inert solvent to the viscous liquid catalysts.

The aluminum catalysts are generally used in the process according to the invention in amounts of about 0.5 to 3 mol %, preferably about 1.0 to 2.5 mol %, based on the allyl alcohol of the formula II employed.

It is possible by means of the process according to the invention, especially on use of the novel mixed aluminum tri(alkyl acetoacetates) of the formula V as catalysts, to prepare the ketones of the general formula I, which are required as essential vitamin precursors, such as 2-methyl-2-hepten-6-one, geranylacetone (6,10-dimethyl-5,9-undecadien-2-one), dihydrogeranylacetone (6,10-dimethyl-5-undecen-2-one), farnesylacetone (6,10,14-trimethyl-5,9,10-pentadecatrien-2-one), 6,10-dimethyl-5-undecen-2-one and dihydrofarnesylacetone (6,10,14-trimethyl-5,10-pentadecadien-2-one), in good yields and good qualities in an industrially straightforward manner.

EXAMPLE 1

Reaction of $Al(O-CH(CH_3)-C_2H_5)_3$ with Methyl Acetoacetate (MAA)

a) 530 g of pure aluminum tri-sec-butoxide were heated to 160° C. in a reaction vessel equipped with a reflux condenser and, while stirring at this temperature, 670 g of MAA were added at a constant rate over the course of two hours (h). In an exothermic reaction, sec-butanol and methanol were liberated but were not removed from the reaction mixture but kept in the reaction mixture by reflux condensation.

After the end of the addition, low boilers were distilled out through a short column with a reflux ratio of 10:1. 150.3 g of alcohol distilled out over the course of 12 h in this way consisted of sec-butanol and methanol. The reaction mixture was then cooled and more alcohol was distilled off under reduced pressure (30 mbar). 860 g of a viscous liquid remained, from which no crystals separated.

A readily pumpable, mobile and stable catalyst solution can be prepared by adding about 140 g of methanol to the residue.

b) For Comparison 530 g of pure aluminum tri-sec-butoxide were heated to 150° C. and then, while stirring and simultaneously distilling out alcohols, 670 g of MAA were pumped in over the course of 2 h. After the end of the addition, distillation was continued for 0.5 h and then the mixture was allowed to cool to 30° C. The residue spontaneously crystallized to solidify to a solid block consisting of aluminum tri(methyl acetoacetate) of low solubility.

EXAMPLE 2

Reaction of Al(—O—CH(CH$_3$)$_2$)$_3$ with MAA 106 g of pure Al(—O—CH(CH$_3$)$_2$)$_3$ were heated to 180° C. in a reaction vessel equipped with a reflux condenser and, while stirring at this temperature, 180 g of MAA were pumped in over the course of 3 h, and the mixture was then refluxed for 1 h. The alcohol which had formed was then distilled out in analogy to Example 1. 199,5 g of a viscous liquid were obtained as residue consisting of an aluminum tri(methyl acetoacetate/isopropyl acetoacetate) mixture. The catalyst obtained in this way remained liquid and pumpable for 50 days and more.

EXAMPLE 3

50,3 g of pure Al(—O—CH(CH$_3$)—C$_2$H$_5$)$_3$ were heated to 150° C. in a reaction vessel equipped with a reflux condenser and, while stirring and heating until refluxing slowly commenced, 72 g of MAA were pumped in over the course of 1 h. The reaction mixture was then refluxed for 15 h to result in 120 g of a low-viscosity stable catalyst solution comprising various aluminum tri(methyl-acetoacetate-sec-butyl acetoacetates) in addition to sec-butanol and methanol.

EXAMPLE 4 a) 39 g of linalool (3,7-dimethyl-1,6-octadien-3-ol) and 3.27 g of the catalyst solution obtained in Example 3, with a content of 0.149 g of Al (4.54% in the liquid catalyst), were heated together to 180° C. Immediately after this temperature was reached, 30.45 g of MAA were pumped in at a constant rate and at an internal temperature of 180±4° C. over the course of 2 h. The exit gas stream was cooled. 6.9 g of low boilers were isolated. The mixture was then stirred at 180° C. for 30 min, cooled and distilled under reduced pressure. 46.55 g of pure E,Z-6,10-dimethyl-5,9-undecadien-2-one (geranylacetone) were obtained. This corresponds to a yield of 95% of theory.

b) For Comparison 39 g of linalool and 1.122 g of aluminum triisopropoxide (with a content of 0.148 g of Al) were heated together to 180° C. and, over the course of 2 h, 30.45 g of MAA were added in analogy to Example 4a).The exit gas stream was cooled, and 5.6 g of CH$_3$OH were trapped. The mixture was then stirred at 180° C. for 30 min, cooled and distilled under reduced pressure. After a small fore-run, 43.23 g of geranylacetone were isolated. This corresponds to a yield of 88% of theory.

EXAMPLES 5 TO 12

Continuous Preparation in a Tubular Reactor a) Description of the Reaction Apparatus (see FIG. 1 for diagram)

The reactions detailed in Table 1 were carried out in a heatable tubular reactor 8 which consisted of two coiled tubes with a lenght of 6 meters (m) and an internal diameter of 6 mm (reactor volume accordingly 340 ml). Aluminum tri-sec-butoxide (100% pure, i.e. without solvent; density 0.97 g/cm$^3$) and methyl acetoacetate (density 1.077 g/cm$^3$) were conveyed by means of the gear pumps 2 and 5, respectively, from the receiving vessels 1 and 4, respectively, through the lines heated by heat exchangers 3 and 6 respectively, into the heatable mixer 7. The two reactants were vigorously mixed at the reaction temperature in the mixer 7 and then transferred into the tubular reactor described above. Downstream of the reactor outlet were disposed the pressure controller 9 by which the required pressure in the system was set, and a cooling section 10 in which the product was cooled to room temperature (RT). The product was then collected in the receiving tank 11 and, after removal of the low boilers by distillation, the degree of transesterification was determined by $^1$H-NMR spectroscopy.

The degree of transesterification was defined in this case as the ratio of the number of 2-butoxy groups to the number of all alkoxy groups, i.e. the total of methoxy groups and 2-butoxy groups.

b) General Description of the Reactions

In the apparatus described above, the amounts of methyl acetoacetate (MAA) and aluminum tri-sec-butoxide (Al (OsecBu)$_3$) which are evident from the following Table 1 were reacted continuously at the temperature evident from Table 1 and under the pressure evident from Table 1, the residence time which was set being evident from Table 1. The resulting product was, after removal of the low boilers (methanol, 2-butanol, methyl acetoacetate), analyzed by $^1$H-NMR spectroscopy.

The degree of transesterification achieved in each case, and the aluminum content, are indicated in Table 1.

The product remained liquid even after storage for several months and can thus advantageously be employed as catalyst for Carroll reactions.

Only in Example 10 did the reaction pressure in conjunction with the residence time not suffice to achieve an adequate degree of transesterification

TABLE 1

| Ex. No. | Reactor volume [ml] | Reactor pressure [bar] | Reactor temperature [° C.] | Residence time [min] | MAA/CAT ratio | MAA feed [ml/min (mmol/min)] | | Al(OsecBu)$_3$ feed [ml/min (mmol/min)] | | Degree of transesterification [%] | Aluminum content [%] |
|---|---|---|---|---|---|---|---|---|---|---|---|
| 5  | 340 | 6   | 150 | 59.69 | 3.07 | 3.22  | (29.9)  | 2.47 | (9.47)  | 47 | 4.4 |
| 6  | 340 | 7   | 150 | 14.82 | 3.08 | 13.0  | (120.6) | 9.95 | (39.18) | 39 | 4.6 |
| 7  | 340 | 6   | 200 | 58.73 | 3.16 | 3.31  | (30.7)  | 2.47 | (9.74)  | 56 | 4.4 |
| 8  | 340 | 6   | 200 | 15.10 | 3.06 | 12.72 | (118.0) | 9.79 | (38.57) | 52 | 4.5 |
| 9  | 340 | 1.2 | 150 | 15.10 | 3.06 | 12.72 | (118.0) | 9.79 | (38.57) | precipitated | — |
| 10 | 340 | 6   | 175 | 37.89 | 3.11 | 5.11  | (47.4)  | 3.87 | (15.23) | 51 | 4.4 |
| 11 | 340 | 6   | 175 | 37.42 | 3.15 | 5.20  | (48.2)  | 3.89 | (15.31) | 52 | 4.3 |
| 12 | 340 | 6   | 175 | 37.42 | 3.15 | 5.20  | (48.2)  | 3.89 | (15.31) | 51 | 4.3 |

EXAMPLES 13 AND 14

Comparison of Tubular Reactor and Loop Reactor for Continuous Preparation a) Reaction in a Tubular Reactor (see FIG. 1 for diagram)

In the apparatus described above, 5.3 g/min (45.7 mmol/min) methyl acetoacetate were reacted continuously with 3.8 g/min (15.5 mmol/min) aluminum tri-sec-butoxide at a temperature of 175° C. under a pressure of 6 bar. The reactor used was the tubular reactor described above, with a residence time of 38 minutes being set. After removal of the low boilers (methanol, 2-butanol, methyl acetoacetate), the product was analyzed by $^1$H-NMR spectroscopy.

The degree of transesterification was 51% and the aluminum content was 4.4%. The product remained liquid even after a storage time of several months.

b) Reaction in a So-called Recycle or Loop Reactor (see FIG. 2 for diagram)

The reactor was carried out under the same reaction conditions (45.7 mmol/min methyl acetoacetate, 15.5 mmol/min aluminum tri-sec-butoxide, reaction temperature=175° C., pressure=6 bar, residence time=38 min), but the reactor described above was modified by returning the reaction mixture leaving the reactor through a three-way tap 12, pump 13 and the line heated by the heat exchanger 14 to the reactor inlet, to form a so-called loop reactor. A recycle ratio of about 20 was set.

The degree of transesterification in this case was 48% and is thus lower than the value achieved in the tubular reactor, and the aluminum content was 4.5%. This product prepared using the loop reactor was also still liquid after storage for several months and could thus advantageously be used as catalyst for Carroll reactions.

EXAMPLE 15

Reaction in a Continuously Stirred Vessel (CSTR)

The mixer and the tubular reactor in the apparatus described above was replaced by a stirred vessel with a reaction volume of 60 ml. Then 0.74 g/min (6.4 mmol/min) methyl acetoacetate (MAA) was reacted continuously with 0.68 g/min (2.13 mmol/min, calc. 100%) of a 77% strength solution of aluminum tri-sec-butoxide (Al(OsecBu)$_3$) in 2-butanol at a temperature of 150° C. under a pressure of 65 bar. The residence time was 42 minutes. After removal of the low boilers, the product was analyzed by $^1$H-NMR spectroscopy. A degree of esterification of 39% was achieved. This value is distinctly below the values achieved in the tubular reactor. Nevertheless, a liquid aluminum catalyst which was stable at room temperature was obtained.

We claim:

1. A process for preparing γ,δ-unsaturated ketones of the formula I comprising:

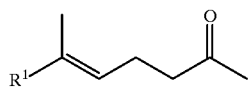
(I)

reacting an allyl alcohol of the formula II

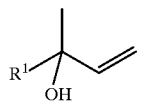
(II)

in which R$^1$ is H or a saturated or unsaturated branched hydrocarbon radical having 1 to 20 carbon atoms, with diketene or an alkyl acetoacetate of the formula III

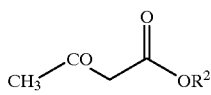
(III)

in which R$^2$ is alkyl having 1 to 5 carbon atoms, in an unmodified or modified Carroll reaction in the presence of an aluminum catalyst of the formula V

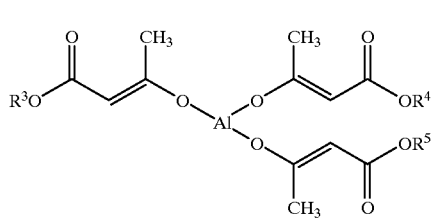
(V)

in which

R$^3$ is an alkyl group having 1–5 carbon atoms;

R$^4$ is an alkyl group having 3 to 10 carbon atoms; and

R$^4$ is an alkyl group having 1 to 10 carbon atoms, where the radicals R$^3$, R$^4$ and R$^5$ can not all have the same meaning.

2. The process of claim 1, wherein R$^3$ is selected from the group consisting of —CH$_3$, —C$_2$H$_5$ and —CH(CH$_3$)—C$_2$H$_5$.

3. The process of claim 1, wherein $R^4$ is selected from the group consisting of —CH(CH$_3$)$_2$, —CH(CH$_3$)—C$_2$H$_5$ and —CH(CH$_3$)—C$_3$H$_7$.

4. The process of claim 1, wherein $R^5$ is selected from the group consisting of —CH$_3$, —C$_2$H$_5$, —CH(CH$_3$)$_2$, —CH(CH$_3$)—C$_2$H$_5$ and —CH(CH$_3$)—C$_3$H$_7$.

5. The process of claim 1, wherein said allyl alcohol is selected from the group consisting of 2-methyl-3-buten-2-ol, linalool, 6,7-dihydrolinalool, nerolidol, 10,11-dihydronerolidol and geranyllinalool.

6. A mixture of aluminum compounds which are liquid at room temperature and have the formula V

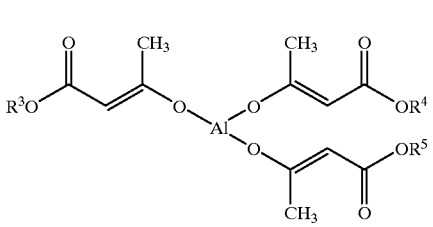

(V)

in which
  $R^3$ is an alkyl group having 1–5 carbon atoms;
  $R^4$ is an alkyl group having 3 to 10 carbon atoms; and
  $R^5$ is an alkyl group having 1 to 10 carbon atoms,
  where the radicals $R^3$, $R^4$ and $R^5$ can not all have the same meaning.

7. The mixture of claim 6, wherein $R^3$ is selected from the group consisting of —CH$_3$ and —C$_2$H$_5$.

8. The mixture of claim 6, wherein $R^4$ is selected from the group consisting of —CH(CH$_3$)$_2$, —CH(CH$_3$)—C$_2$H$_5$, C(CH$_3$)$_3$ and —CH(CH$_3$)—C$_3$H$_7$.

9. The mixture of claim 6, wherein $R^5$ is selected from the group consisting of —CH$_3$, —C$_2$H$_5$, —CH(CH$_3$)$_2$, —CH(CH$_3$)—C$_2$H$_5$ and —CH(CH$_3$)—C$_3$H$_7$.

10. A process for preparing mixtures, which are liquid at room temperature, of aluminum compounds of the formula V as claimed in claim, 6, which comprises heating aluminum alcoholates of the formula VI

Al(O—R$^6$)$_3$    (VI), in which $R^6$ is an alkyl group having 2 to 10 carbon atoms, with at least 3 mol of an alkyl acetoacetate of an alcohol different from R$^6$OH per mole of aluminum alcoholate, without removing the alcohol liberated in the reaction during the heating from the reaction mixture.

11. The process of claim 10, wherein $R^6$ is selected from the group consisting of —CH(CH$_3$)$_2$, CH(CH$_3$)—C$_2$H$_5$, —C(CH$_3$)$_3$ and —CH(CH$_3$)—C$_3$H$_7$.

12. A process for preparing mixtures, which are liquid at room temperature, of aluminum compounds of the formula V as claimed in claim 6, which comprises heating aluminum alcoholates of the formula VI

Al(O—R$^6$)$_3$    (VI), in which $R^6$ is an alkyl group having 2 to 10 carbon atoms, with at least 3 mol of a mixture of at least 2 different alkyl acetoacetates.

13. The process of claim 12, wherein $R^6$ is selected from the group consisting of —CH(CH$_3$)$_2$, —CH(CH$_3$) —C$_2$H$_5$, —C(CH$_3$)$_3$ and—CH(CH$_3$)—C$_3$H$_7$.

14. A process for the continuous preparation of aluminum compounds which are liquid at room temperature of the formula V

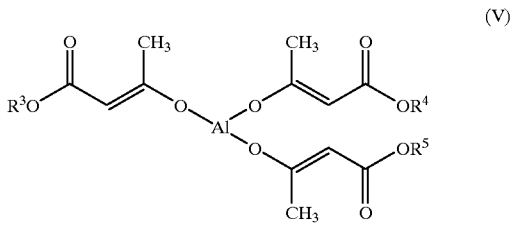

(V)

in which
  $R^3$ is an alkyl group having 1–5 carbon atoms;
  $R^4$ is an alkyl group having 3 to 10 carbon atoms; and
  $R^5$ is an alkyl group having 1 to 10 carbon atoms,
  where the radicals $R^3$, $R^4$ and $R^5$ can not all have the same meaning which comprises reacting in each case
  i) one mol of an aluminum alcoholate of the formula VI

Al(O—R$^6$)$_3$    (VI), in which $R^6$ is an alkyl group having 2 to 10 carbon atoms; and
  ii) 3 to 10 mol of an alkyl acetoacetate of the formula III

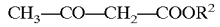

CH$_3$—CO—CH$_2$—COOR$^2$    (III), in which $R^2$ is alkyl having 1 to 5 carbon atoms, wherein $R^2$ and $R^6$ are different or with at least 3 mol of a mixture of 2 or 3 different alkyl acetoacetates of the formula III in pure form or dissolved in a suitable inert solvent, continuously at temperatures from 100 to 250° C., under a pressure of from 1 to 100 bar, and with residence times of from 5 to 120 minutes, it being necessary to choose from pressure and temperature so that no gas phase can form in the reaction vessel.

15. The process of claim 14, wherein $R^3$ is selected from the group consisting of —CH$_3$, —C$_2$H$_5$ and —CH(CH$_3$)—C$_2$H$_5$.

16. The process of claim 14, wherein $R^4$ is selected from the group consisting of —CH(CH$_3$)$_2$, —CH(CH$_3$)—C$_2$H$_5$ and —CH(CH$_3$)—C$_3$H$_7$.

17. The process of claim 14, wherein $R^5$ is selected from the group consisting of —CH$_3$, —C$_2$H$_5$, —CH(CH$_3$)$_2$, —CH(CH$_3$)—C$_2$H$_5$ and —CH(CH$_3$)—C$_3$H$_7$.

18. The process of claim 14, wherein $R^6$ is selected from the group consisting of CH$_2$—CH(CH$_3$)$_2$, CH(CH$_3$)—C$_2$H$_5$ and —CH(CH$_3$)—C$_3$H$_7$.

19. The process of claim 14, wherein $R^2$ is selected from the group consisting of —CH$_3$, —C$_2$H$_5$, —CH(CH$_3$)—C$_2$H$_5$ and —CH$_2$—CH(CH$_3$)$_2$.

20. The process of claim 14, wherein said temperature is 150 to 200° C.

21. The process of claim 14, wherein said pressure is 1 to 10 bar.

22. The process of claim 14, wherein said residence time is 15 to 45 minutes.

23. A process as claimed in claim 14, wherein said aluminum alcoholate of formula VI is mixed with said alkyl acetoacetate or said alkyl acetoacetates of formula III continuously under elevated pressure and at elevated temperature in a mixer and then reacted in a reactor with tubular characteristics.

* * * * *